(12) United States Patent
Cavallo et al.

(10) Patent No.: US 6,319,517 B1
(45) Date of Patent: Nov. 20, 2001

(54) PHARMACEUTICAL PREPARATION COMPRISING LYOPHILIZED LIPOSOMES ENCAPSULATING AN ACTIVE PRINCIPLE WHICH IS HIGHLY INSOLUBLE IN WATER, AND THE PROCESS FOR PREPARING THE SAID PREPARATION

(75) Inventors: Giovanni Cavallo, Ostia; Leonardo Marchitto, Cupra Marittima, both of (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 09/367,715

(22) PCT Filed: Feb. 12, 1998

(86) PCT No.: PCT/EP98/00817

§ 371 Date: Nov. 3, 1999

§ 102(e) Date: Nov. 3, 1999

(87) PCT Pub. No.: WO98/36736

PCT Pub. Date: Aug. 27, 1998

(30) Foreign Application Priority Data

Feb. 20, 1997 (IT) .............................. MI97A0362

(51) Int. Cl.$^7$ ...................................................... A61K 9/127
(52) U.S. Cl. ..................... 424/450; 424/1.21; 424/9.321; 424/9.51; 424/417; 264/4.1; 264/4.3; 514/2; 514/8; 514/21
(58) Field of Search ................................... 424/450, 1.21, 424/9.321, 9.51, 417, 94.3; 264/4.1, 4.3; 514/2, 8, 21; 935/54

(56) References Cited

U.S. PATENT DOCUMENTS

| 5,567,433 | * | 10/1996 | Collins | 424/450 |
| 5,683,714 | * | 11/1997 | Adler-Moore | 424/450 |
| 5,817,336 | * | 10/1998 | Schmidt | 424/450 |

OTHER PUBLICATIONS

Crowe BBA 939 p 327–334, 1988.*
Crowe ABB 242 #1 pp 240–247, 1985.*

* cited by examiner

*Primary Examiner*—Gollamudi S. Kishore
(74) *Attorney, Agent, or Firm*—Oblon, Spivak, McClelland, Maier & Neustadt, P.C.

(57) ABSTRACT

The present invention to relates to a pharmaceutical preparation comprising lyophilized liposomes encapsulating a biologically-active principle which is highly insoluble in water and stable over time.

12 Claims, No Drawings

PHARMACEUTICAL PREPARATION COMPRISING LYOPHILIZED LIPOSOMES ENCAPSULATING AN ACTIVE PRINCIPLE WHICH IS HIGHLY INSOLUBLE IN WATER, AND THE PROCESS FOR PREPARING THE SAID PREPARATION

This application is a 371 of PCT/EP98/00817 filed on Feb. 12, 1998.

The invention relates to a pharmaceutical preparation comprising lyophilized liposomes encapsulating a biologically-active principle which is highly insoluble in water, and a process for preparing the said preparation.

More particularly, the invention relates to a pharmaceutical preparation comprising lyophilized liposomes encapsulating a biologically-active principle which is highly insoluble in water and stable over time.

In the course of the present description and the Claims, the term "highly insoluble in water" is used to describe all those compounds having a solubility in water $\leq 0.01\%$ (w/v).

It is known that the use of liposomes in medical treatments has been held back by difficulties encountered in obtaining pharmaceutical preparations which are sufficiently stable both during lyophilization and over time. The said difficulties consist above all in the preparation of liposomes which neither burst nor pack together. In other words, the liposomes should remain whole and separate from one another.

The structural integrity of the liposomes is also particularly important in the case where the active principle is highly insoluble in water. In point of fact, the bursting of the liposomes during lyophilization and/or during preservation does not prevent the water-soluble active principles from going into solution when the aqueous liposome solution is reconstituted before administration to the patient by the addition of physiological solution. On the other hand, in the case of the bursting of liposomes comprising active principles which are highly insoluble in water, reconstitution of the lyophilisate yields a solution comprising less active principle than required. The greater the quantity of burst liposomes, the greater the difference between the theoretical and the actual quantity of active principle in solution.

A lyophilization method of liposomes comprising a water-soluble biologically-active principle is described by U.S. Pat. No. 4,857,319. This document describes the lyophilization of liposomes preferably of an average size of about 50–100 nm, with the addition, as a preserving agent, of a disaccharide on the inside only (with the liposome content encapsulated), or on the outside only, or on both the inside and the outside. The disaccharide/lipid weight ratio ranges between 0.1:1 and 4:1. Preferably, the disaccharide is trehalose. The freezing phase is carried out at the temperature of liquid nitrogen (−195.8° C.).

In the aforementioned patent, stability characteristics during lyophilization were evaluated by means of measurements of retention of the active principle encapsulated in the liposomes after reconstitution of the lyophilisate via rehydration.

Table 2 of the aforementioned patent shows that retention is high (99–100%) only when the trehalose/lipid ratio is greater than 1.76 and the trehalose is present both on the inside and the outside of the liposomes. When the said ratio is equal to 0.11 and to 0.19, retention is equal to 22% and 49%, respectively, even if the trehalose is present both on the inside and the outside of the liposomes. By contrast, when the trehalose is present only on the outside, the amount of active principle retained is drastically reduced, even for very large quantities of trehalose. In point of fact, with a trehalose/lipid ratio of 3.9, the amount retained is only 26%.

Nevertheless, the aforementioned results are not reproducible when the biologically-active principle is highly insoluble in water. In fact, when the trehalose is added during preparation of the liposomes in order to encapsulate it within the lipid vesicles, a non-homogeneous, non-extrudible suspension is obtained (Preparations for Comparison 1 and 2).

Surprisingly, it has been discovered that liposomes comprising a biologically-active principle which is highly insoluble in water remain substantially whole during lyophilization when the trehalose is added in small quantities to the liposomes before lyophilization only, and the said iyophilization is effected by carrying out the freezing phase at a temperature of between −5° and −70° C.

It is an object of the present invention to provide a lyophilized composition comprising trehalose and lipid liposomes in which a biologically-active principle has been incorporated, characterized in that the biologically-active principle is highly insoluble in water, the trehalose/lipid weight ratio is $\leq 1.5$, and all of the trehalose was added to the outside of the liposomes already formed before lyophilization.

After reconstitution by rehydration, the said composition retains in solution more than 95% of the biologically-active principle which is highly insoluble in water (Examples 1, 2 and 3).

Typical examples of biologically-active principles which are highly insoluble in water are: lonidamine, melatonin, cyclosporin A and bindarit.

The lipids of the liposome composition to be subjected to the lyophilization process according to the invention are preferably chosen from the group comprising phosphoglycerides, glycerides, diglycerides, triglycerides, phospholipids, galactosyl and glucosyl lipids, cholesterol and its derivatives, sphingolipids and their mixtures. Preferably, the lipids are phospholipids. The trehalose/lipid weight ratio, in turn, preferably lies between 1:2 and 1:1.

The average size of the liposomes may be between 50 and 250 nm. Preferably, it is between 50 and 100 nm.

A second object of the invention is constituted by a lyophilization process, characterized in that:
1) from 0.2 to 1.5 parts in weight of trehalose are added for each part in weight of lipids of an aqueous liposome composition in which the average size of the liposomes lies between 50 and 250 nm, and the said liposomes comprise a biologically-active principle which is highly insoluble in water;
2) the said composition is chilled via the lyophilizer chilling-plate to a temperature between −5° and −70° C., at a chilling rate of between 0.5° and 2° C./min.;
3) once the predetermined freezing temperature is reached, the said composition is kept at the said temperature for a period of between 2 and 5 hours;
4) a vacuum of between $5 \times 10^{-1}$ and $8 \times 10^{-2}$ millibar is applied, leaving the temperature of the chilling plate at the chilling temperature defined in point 2) for a period lasting between 2 and 5 hours;
5) the temperature of the chilling plate is brought to −1 50° C., and kept there until the water is completely removed.

The preferred operating conditions are as follows:

Phase 2 freezing temperature: −20° to −30° C.

chilling rate: 0.77° C./min.

Phase 3
time: 3 hours
Phase 4
vacuum: $6 \times 10^{-2}$ millibar
Phase 5
a) When the freezing temperature (Phase 2) is below −15° C., the temperature of the chilling plate is increased to −15° C. at a rate of between 0.5° and 2° C. and lyophilization takes place for 20 hours; then the temperature of the chilling plate is brought to −10° C., and after an hour to +5° C., and lyophilization occurs for 16 hours.
b) When the freezing temperature (Phase 2) is greater than or equal to −15° C., lyophilization is continued for 20 hours, after which the temperature of the chilling plate is taken to +5° C. and lyophilization occurs for 16 hours.

A particularly preferred liposome composition according to the invention comprises:

Component % (w/w)
phosphatidylcholine : 94
lysophosphatidylcholine : 3
N-acyl-ethanolamine : 1
phosphatidyl ethanolamine : 0.1
triglycerides : 1
free fatty acids : 0.75
DL-α-tocopherol : 0.15

Typically, the aqueous pharmaceutical liposome composition of the invention is prepared by:
a) dispersing a biologically-active principle which is highly insoluble in water in lipids at a temperature of between 20° and 30° C.;
b) suspending the said dispersion in an aqueous phase;
c) letting the said suspension stand at ambient temperature for a period of between 0 and 48 hours;
d) heating to between 30° and 75° C. for 10–40 minutes;
e) freezing to between −150° and −2000° C.;
f) repeating phases d) and e) at least twice, and not more than 8 times;
g) filtering through a filtering membrane with pores of 500–1000 nm diameter;
h) extruding through a membrane with pores of 50–400 nm diameter; and simultaneous
i) elimination of the active principle not trapped.

The duration of phase c) depends on the quantity of active principle highly insoluble in water which it is wished to trap in the liposomes. The person skilled in the art will thus have no difficulty in determining by means of a few simple routine experiments the suitable time for each type of active principle and liposome composition.

Preferably, the aqueous phase consists of a 0.05%–0.9% (w/v) aqueous solution of sodium chloride. Typically, the amount of lipids used is 0.01–0.4 parts in weight for each part in weight of aqueous solution. In its turn, the amount of active principle generally lies between 0.01 and 0.3 parts in weight for each part in weight of lipids.

Generally, extrusion is effected using as an extrusion gas either compressed air or an inert gas chosen from the group comprising nitrogen, helium and argon. Preferably, helium is the inert gas. Pressure in the extrusion phase is preferably between 500 and 5500 kPa, and the temperature lies preferably between 20° and 750° C., even more preferably between 40° and 65° C. Typical examples of suitable extruders are the Lipex Biomembranes Thermobarrel Extruder type, or the Emulsiflex CC Avestin with Costar™ polycarbonate membrane with pores of between 50 and 600 nm in diameter.

Proceeding as described above, aqueous liposome compositions are obtained comprising about 8 mg/ml of melatonin, 3.8 mg/ml of lonidamine, 1 mg/ml of cyclosporin A and 4 mg/ml of bindarit against a water-solubility of $3 \times 10^{-3}$ mg/ml (lonidamine), $1 \times 10^{-1}$ mg/ml (bindarit) and, practically, the absolute insolubility of melatonin (G. S. Shida et al. "J. Pineal Res." 1994, 16, 198–201) and of cyclosporin A ["Insoluble in Water", a monograph of cyclosporin A in "Analytical Profiles of Drug Substances", 16, 163, (1987)].

The following examples shall serve to illustrate the present invention, without, however, limiting it.

PREPARATION I

A liposome composition comprising a biologically-active principle which is highly insoluble in water was prepared as described below.

100 mg of melatonin were dispersed in 1 g of phospholipids at 30° C. for 10 minutes by means of a Ultraturrax™-type homogenizer. Directly afterwards, the said dispersion was suspended in 10 ml of 0.9% (w/v) aqueous solution of sodium chloride by means of the said homogenizer and then heated in a water-bath at 55° C. for 20 minutes.

The suspension thus obtained was subjected to the following chilling and heating cycle:
chilling in liquid nitrogen for 1 minute,
heating at 55° C. until complete fluidization of the phospholipids.

The said cycle was repeated 6 times.

The suspension was passed twice through a 0.6 μm filter using the Lipex Biomembranes device.

A "Multilamellar Large Vesicle" (MLV) suspension was thus obtained and subjected to 6 continuous-extrusion cycles using a 10-mi Lipex Biomembranes Thermobarrel type extruder with 0.1 μm Costar™ polycarbonate filters at 55° C., using helium as an extrusion gas at a pressure of between 1000 and 4800 kPa.

PREPARATION II

We proceeded as described for Preparation I, using 2 g of phospholipids and 50 mg of lonidamine in place of 1 g of phospholipids and 100 mg of melatonin.

PREPARATION III

We proceeded as described for Preparation I, using 2 g of phospholipids and 200 mg of melatonin in place of 1 g of phospholipids and 100 mg of melatonin.

PREPARATION IV

We proceeded as described for Preparation II, except that extrusion was carried out through a 0.2 μm in place of a 0.1 μm polycarbonate membrane.

PREPARATION V 30 mg of cyclosporin A were dispersed in 2 g of phospholipids at 30° C. for 10 minutes by means of an Ultraturrax™-type homogenizer. Directly afterwards, the said dispersion was suspended in a 0.9% (w/v) aqueous solution of sodium chloride using the said homogenizer, and left standing at ambient temperature for 24 hours. Following this, the suspension obtained was heated in a water bath at 65° C. for 20 minutes.

The suspension thus obtained was subjected to the following chilling and heating cycle:
chilling in liquid nitrogen for 1 minute,
heating at 65° C. until complete fluidization of the phospholipids.

The said cycle was repeated 6 times.

The suspension was passed twice through a 0.6 μm filter using the Lipex Biomembranes device.

A "Multilamellar Large Vesicle" (MLV) suspension was thus obtained and subjected to 6 continuous-extrusion cycles using a 10-ml Lipex Biomembranes Thermobarrel type extruder with 0.1 μm Costar™ polycarbonate filters at 65° C., using helium as an extrusion gas at a pressure of between 1000 and 4800 kPa.

PREPARATION VI

We proceeded as described for Preparation I, using 2 g of phospholipids and 50 mg of bindarit in place of 1 g of phospholipids and 100 mg of melatonin.

PREPARATION FOR COMPARISON 1

Preparation 1A 100 mg of melatonin and 1 g of trehalose were dispersed in 1 g of phospholipids at 30° C. for 10 minutes by means of an Ultraturrax™-type homogenizer. Directly afterwards, the said dispersion was suspended in 10 ml of 0.9% (w/v) aqueous solution of sodium chloride using the said homogenizer, and then heated in a water-bath at 55° C. for 20 minutes.

The suspension thus obtained was subjected to the following chilling and heating cycle:

chilling in liquid nitrogen for 1 minute, heating at 55° C. until complete fluidization of the phospholipids.

The said cycle was repeated 6 times.

The suspension was passed twice through a 0.6 μm filter using the Lipex Biomembranes device.

In this manner, a very dense mass was obtained. The attempt to extrude it by means of a 10-ml Lipex Biomembranes Thermobarrel type extruder with 0.1-μm Costar™ polycarbonate filters at 55° C. using helium as an extrusion gas at a pressure of between 1000 and 4800 kPa, was unsuccessful.

Preparation 1B

We proceeded as described for the preceding Preparation 1A, except that the melatonin was omitted. A "Multilamellar Large Vesicle" (MLV) suspension was obtained which turned out to be perfectly extrudible by means of a 10-ml Lipex Biomembranes Thermobarrel type extruder with 0.1 μm Costar™ polycarbonate filters at 55° C., using helium as an extrusion gas at a pressure of between 1000 and 4800 kPa.

PREPARATION FOR COMPARISON 2

Preparation 2A

We proceeded as described for the purposes of the Preparation for Comparison 1A, except that 2 g of phospholipids were used instead of 1.

In this case also, a very dense, non-extrudible mass was obtained.

Preparation 2B

We proceeded as described for the preceding Preparation for Comparison 1B, except that 2 g of phospholipids were used instead of 1.

In this case also, a perfectly extrudible MLV suspension was obtained.

EXAMPLE 1

Preparation II was divided up into 1-ml aliquots, and to each aliquot was added trehalose according to the trehalose/lipid weight ratio given in Table 1/1.

Lyophilization was carried out in a plate lyophilizer, as follows:

1) chilling to −25° C. at the rate of 0.77° C./min.;
2) maintaining the said temperature (−25° C.) for 3 hours,
3) application of the vacuum ($6\times10^{-2}$ millibar) and maintenance at the said temperature (−25° C.) for 2 hours;
4) heating to −15° C. for 20 hours under a vacuum of $6\times10^{-2}$ millibar;
5) heating to −10° C. for 2 hours under a vacuum of $6\times10^{-2}$ millibar;
6) heating to +5° C. for 20 hours under a vacuum of $6\times10^{-2}$ millibar;
7) locking the vacuum;
8) introduction of air.

The lyophilisate (1 ml) was rehydrated with 1 ml of distilled water and kept at ambient temperature for 30 minutes in order to permit the efficient reconstruction of the liposomes.

0.5 ml of the said solution was further diluted with 10 ml of physiological solution in order to measure the average size of the liposomes with the NICOMP 370 device.

Table 1/1 shows the results obtained.

TABLE 1/1

Average size of the liposomes before and after lyophilization

| Batch | Trehalose/lipids (w/w) | Before | After |
|---|---|---|---|
| LM/302 | 0 | 102 | 911.7 |
|  | 1:2 | 102 | 115.9 |
|  | 1:1 | 102 | 109.7 |
|  | 2:1 | 102 | 167.9 |
| LM/303 | 0 | 99.2 | 911.7 |
|  | 1:2 | 99.2 | 98.7 |
|  | 1:1 | 99.2 | 109.8 |
|  | 2:1 | 99.2 | 291.3 |
| LM/304 | 0 | 98.6 | 911.8 |
|  | 1:2 | 98.6 | 94.9 |
|  | 1:1 | 98.6 | 105.8 |
|  | 2:1 | 98.6 | 794 |

From Table 1/1 we can see that the absence of trehalose entails a certain degree of fusion of the liposomes, evidenced by the increase in their average size. Surprisingly, the increase in the amount of trehalose (trehalose/lipids 2:1) also causes a certain degree of fusion with a consequent increase in the average size.

Similar results have also been obtained with Preparation IV.

The average size of the liposomes and the lonidamine amount were determined from a certain number of samples, freshly prepared as described above. Subsequently, the samples were replaced in the refrigerator at 5° C. and sampled at given intervals, rehydrated to determine the amount of the active principle and the average size of the liposomes. The results thus obtained are given in Table 1/2.

TABLE 1/2

Trehalose/lipid ratio (w/w) 1:2

| Batch | Time (months) | HPLC amount (mg/ml) | Average size (nm) |
|---|---|---|---|
| LM/328 | $t_0$ | 3.3 | 107 |
|  | 1 | 3.2 | 110 |
|  | 3 | 3.2 | 114 |
|  | 6 | 3.1 | 127.2 |
| LM/329 | $t_0$ | 3.2 | 103.3 |
|  | 1 | 3.2 | 101 |
|  | 3 | 3.2 | 110.5 |
|  | 6 | 3.1 | 115 |
| LM/330 | $t_0$ | 3.3 | 99.2 |
|  | 1 | 3.4 | 99.5 |
|  | 3 | 3.2 | 100.5 |
|  | 6 | 3.1 | 113.6 |

EXAMPLE 2

Preparation III was lyophilized as described in Example 1 above, and the average size of the liposomes before and after lyophilization (Table 2/1), as well as the average size of the liposomes and the amount of melatonin in the fresh preparations and in those kept at 5° C., were determined as described in the aforementioned example (Table 2/2).

TABLE 2/1

Average size of the liposomes before and after lyophilization

| Batch | Trehalose/lipids (w/w) | Before | After |
|---|---|---|---|
| LM/336 | 0 | 92 | 16953 |
|  | 1:2 | 92 | 6875 |
|  | 1:1 | 92 | 96.5 |
|  | 2:1 | 92 | 109.7 |
| LM/337 | 1:2 | 92 | 146.3 |
|  | 1:1 | 92 | 98.8 |
|  | 2:1 | 92 | 8319.8 |
| LM/338 | 1:2 | 92 | 179.7 |
|  | 1:1 | 92 | 225.7 |
|  | 2:1 | 92 | 2984 |

Similar results were also obtained with Preparation 1.

TABLE 2/2

Trehalose/lipid ratio (w/w) 1:1

| Batch | Time (months) | HPLC amount (mg/ml) | Average size (nm) |
|---|---|---|---|
| LM/359 | $t_0$ | 6 | 104 |
|  | 1 | 6 | 103.2 |
|  | 3 | 5.8 | 109.5 |
| LM/360 | $t_0$ | 6.5 | 107.2 |
|  | 1 | 6.5 | 106.3 |
|  | 3 | 6.7 | 113.6 |
| LM/361 | $t_0$ | 6.2 | 98.4 |
|  | 1 | 6.3 | 99 |
|  | 3 | 6 | 100.5 |

EXAMPLE 3

Preparation VI was lyophilized as described in Example 1 above, and the average size of the liposomes before and after lyophilization (Table 3/1) as well as the average size of the liposomes and the amount of the bindarit in the fresh preparations and in those kept at 5° C., were determined as described in the aforementioned Example (Table 3/2).

TABLE 3/1

Average size of the liposomes before and after lyophilization

| Batch | Trehalose/lipids (w/w) | Before | After |
|---|---|---|---|
| LM/342 | 0 | 102.7 | 7524.1 |
|  | 1:2 | 102.7 | 928 |
|  | 1:1 | 102.7 | 109 |
|  | 2:1 | 102.7 | 140 |
| LM/343 | 1:2 | 102.7 | 546.6 |
|  | 1:1 | 102.7 | 112.3 |
|  | 2:1 | 102.7 | 1559.2 |
| LM/344 | 1:2 | 102.7 | 194.9 |
|  | 1:1 | 102.7 | 112.2 |
|  | 2:1 | 102.7 | 4722 |

TABLE 3/2

Trehalose/lipid ratio (w/w) 1:1

| Batch | Time (months) | HPLC amount (mg/ml) | Average size (nm) |
|---|---|---|---|
| LM/356 | $t_0$ | 3.2 | 135.4 |
|  | 1 | 3.1 | 128 |
|  | 3 | 3.2 | 131.3 |
| LM/357 | $t_0$ | 3.1 | 122 |
|  | 1 | 3.1 | 121 |
|  | 3 | 3.2 | 126.2 |
| LM/358 | $t_0$ | 3.1 | 126 |
|  | 1 | 3.1 | 122.8 |
|  | 3 | 2.9 | 121.8 |

EXAMPLE FOR COMPARISON 1

Preparation II was divided into 1 ml aliquots and trehalose was added to each aliquot according to the trehalose/lipid weight ratio given in Comparison Table 1.

The Preparation was then frozen at the temperature of liquid nitrogen (−195.8° C.) and lyophilized for 20 hours, with no external temperature control.

lyophilized (1 ml) was rehydrated with 1 ml of distilled water and kept at ambient temperature for 2 hours.

0.5 ml of the said solution was further diluted with 10 ml of physiological solution in order to measure the average size of the liposomes with the NICOMP 370 device.

The results obtained are illustrated in Comparison Table 1 below.

COMPARISON TABLE 1

Average size of the liposomes before and after lyophilization

| Batch | Trehalose/lipids (w/w) | Before | After |
|---|---|---|---|
| LM/302 | 0 | 102 | 911.8 |
|  | 1:2 | 102 | 254.8 |
|  | 1:1 | 102 | 219.3 |
|  | 2:1 | 102 | 773.7 |
| LM/303 | 0 | 99.2 | 911.8 |
|  | 1:2 | 99.2 | 349.9 |
|  | 1:1 | 99.2 | 180.4 |
|  | 2:1 | 99.2 | 717.2 |
| LM/304 | 0 | 98.6 | 911.8 |
|  | 1:2 | 98.6 | 722.5 |
|  | 1:1 | 98.6 | 161.1 |
|  | 2:1 | 98.6 | 150 |

From Comparison Table 1 we can observe that when lyophilization is carried out at the temperature of liquid nitrogen, either in the absence of trehalose or in the presence of trehalose in the ratios given in the Table above, a certain degree of fusion of the liposomes takes place, evidenced by the increase in their average size. In addition, the above data indicate that when lyophilization is carried out at the temperature of liquid nitrogen, the course of the lyophilization itself (for preparations of the same composition) does not always reproduce the same results.

What is claimed is:

1. Lyophilized composition comprising trehalose and lipid liposomes in which a biologically-active principle has been incorporated, wherein the biologically-active principle is highly insoluble in water, the trehalose/lipid weight ratio is between 2:1 and 1:2, and all of the trehalose was added to the outside of the liposomes already formed before lyophilization.

2. Lyophilized composition according to claim 1, wherein the biologically-active principle is selected from the group consisting of lonidamine, melatonin, cyclosporin A and bindarit.

3. Lyophilized composition according to claim 1, wherein the lipids are selected from the group consisting of phosphoglycerides, glycerides, diglycerides, triglycerides, phospholipids, galactosyl lipids, glucosyl lipids, cholesterol, cholesterol derivatives, sphingolipids and their mixtures.

4. Lyophilized composition according to claim 3, wherein the lipids are phospholipids.

5. Lyophilized composition according to claim 1, wherein the trehalose/lipid weight ratio is between 1:2 and 1:1.

6. Lyophilized composition according to claim 1, wherein the average size of the liposomes is between 50 and 250 nm.

7. Lyophilized composition according to claim 6, wherein the average size of the liposomes is between 50 and 100 nm.

8. Process for lyophilizing a composition comprising trehalose and lipid liposomes, in which there has been incorporated a biologically-active principle:
   a) adding trehalose to the liposome wherein the ratio of the trehalose to liposome is between 1:2 and 2:1, wherein the average size of the liposomes is between 50 and 250 nm, the said liposomes comprising a biologically-active principle which is highly insoluble in water;
   b) the said composition is chilled by means of the chilling plate of the lyophilizer to a temperature between $-5°$ and $-70°$ C., at a chilling rate of between $0.5°$ and $2°$ C./min.;
   c) once the predetermined freezing temperature has been reached, the said composition is kept at the said temperature for between 2 and 5 hours;
   d) a vacuum of between $5 \times 10^{-1}$ and $8 \times 10^{-2}$ millibar is applied, leaving the temperature of the chilling plate at the chilling temperature defined in point b) for a period of between 2 and 5 hours;
   e) the temperature of the chilling plate is brought to $-15°$ C., and kept there until the water is completely removed.

9. Lyophilization process according to claim 8, wherein, in Phase b), the freezing temperature is between $-20°$ and $-30°$ C.

10. Lyophilization process according to claim 8, wherein, in Phase b), the chilling rate is $0.77°$ C./min.

11. Lyophilization process according to claim 8, wherein, in Phase c), the time is 3 hours.

12. Lyophilization process according to claim 8, wherein, in Phase d), the vacuum is $6 \times 10^{-2}$ millibar.

* * * * *